(12) United States Patent
Oikawa et al.

(10) Patent No.: US 7,067,699 B2
(45) Date of Patent: Jun. 27, 2006

(54) METHOD FOR PRODUCING CYCLOHEXANONE OXIME

(75) Inventors: Miyuki Oikawa, Niihama (JP); Masami Fukao, Ritto (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/817,923

(22) Filed: Apr. 6, 2004

(65) Prior Publication Data

US 2004/0204609 A1  Oct. 14, 2004

(30) Foreign Application Priority Data

Apr. 9, 2003 (JP) ............................. 2003-104900

(51) Int. Cl.
*C07C 549/00* (2006.01)
(52) U.S. Cl. ................................................ 564/267
(58) Field of Classification Search ................ 564/267
See application file for complete search history.

(56) References Cited

U.S. PATENT DOCUMENTS

| 4,745,221 A | | 5/1988 | Roffia et al. |
| 5,227,525 A | * | 7/1993 | Tonti et al. ............... 564/267 |
| 5,312,987 A | | 5/1994 | Mantegazza et al. |
| 5,451,701 A | | 9/1995 | Zajacek et al. |
| 5,498,793 A | | 3/1996 | Mantegazza et al. |
| 5,599,987 A | * | 2/1997 | Crocco et al. ............... 564/267 |
| 5,683,952 A | | 11/1997 | Onozawa et al. |
| 5,736,479 A | * | 4/1998 | Schodel et al. ............... 502/77 |
| 2003/0228970 A1 | | 12/2003 | Sun et al. |

FOREIGN PATENT DOCUMENTS

| EP | 0 690 045 A1 | 1/1996 |
| EP | 0 735 017 A1 | 10/1996 |
| IT | EP 0 496 385 A1 | 7/1992 |
| IT | EP 0 564 040 A2 | 10/1993 |
| JP | 6-49015 A | 2/1994 |
| JP | 6-92922 A | 4/1994 |
| JP | 6-259256 A | 9/1994 |
| JP | 7-100387 A | 4/1995 |
| JP | EP 1 375 473 A1 | 1/2004 |

* cited by examiner

*Primary Examiner*—Johann Richter
*Assistant Examiner*—Chukwuma Nwaonicha
(74) *Attorney, Agent, or Firm*—Birch, Stewart, Kolasch & Birch, LLP

(57) ABSTRACT

In producing cyclohexanone oxime by a method comprising the step of reacting cyclohexanone, hydrogen peroxide and ammonia in the presence of titanium silicate, a brand-new titanium silicate and a recycled titanium silicate which has been recovered from a production method of cyclohexanone oxime are used. In accordance with the present invention, cyclohexanone is subjected to ammoximation by hydrogen peroxide and ammonia with suppressing the degradation- of titanium silicate as a catalyst, to produce cyclohexanone oxime with a high yield.

7 Claims, No Drawings

METHOD FOR PRODUCING CYCLOHEXANONE OXIME

BACKGROUND OF THE INVENTION

1. Technical Field of the Invention

The present invention relates to a method for producing cyclohexanone oxime by ammoximation of cyclohexanone. Cyclohexanone oxime is useful as a starting material for producing ε-caprolactam, or the like.

2. Related Art

For producing cyclohexanone oxime, there has been proposed a method of subjecting cyclohexanone to ammoximation with hydrogen peroxide and ammonia in the presence of titanium silicate catalyst (e.g., Japanese Patent Application Laid-Open No. (JP-A-) 62-59256, JP-A-6-49015, JP-A-6-92922, and JP-A-7-100387).

Such a method has advantages in that it does not need to neutralize sulfuric acid with ammonia, while the neutralization is conducted in the conventional method of ammoximation with hydroxylamine sulfate, and in that product separation from the catalyst can be easily carried out since a solid catalyst is utilized.

However, in the above ammoximation reaction, the catalytic activity of the titanium silicate catalyst is gradually deteriorated with the passage of reaction time so that the conversion rate of cyclohexanone and the selectivity to cyclohexanone oxime may become insufficient. As a result, the yield of cyclohexanone oxime tends to be lowered.

In order to maintain a desired yield of cyclohexanone oxime, it is necessary to exchange the catalyst which has been used to some extent to be degraded, with a brand-new catalyst. If such a degradation of the catalyst can be suppressed, the frequency of the catalyst exchange can be reduced, and therefore, the method has advantages in view of catalyst cost.

SUMMARY OF THE INVENTION

The present inventors have studied on the above ammoximation reaction from the viewpoint of catalyst-cost reduction for the purpose of suppressing degradation of a titanium silicate catalyst, especially, reducing an inactivation of the catalytst, thereby suppressing the lowering of yield of cyclohexanone oxime. As a result, it has been found that the above object and other objects can be achieved by utilizing a recycled catalyst together with a brand-new catalyst in the reaction system, and the present invention has been accomplished.

The present invention provides a method for producing a cyclohexanone oxime, the method comprising the step of reacting cyclohexanone, hydrogen peroxide and ammonia in the presence of a brand-new titanium silicate and a recycled titanium silicate, wherein the recycled titanium silicate is a titanium silicate which has been recovered from a method comprising the step of reacting cyclohexanone, hydrogen peroxide and ammonia in the presence of titanium silicate.

DETAILED DESCRIPTION OF THE INVENTION

A titanium silicate to be used in the present invention may be a zeolite comprising titanium, silicon and oxygen as elements in its skeletal structure. The titanium silicate may have a skeletal structure substantially constituted of titanium, silicon and oxygen, or a skeletal structure further containing (an) optional element(s) other than these elements.

A preferable titanium silicate is a titanium silicate having an atomic ratio of silicon to titanium of from 10 to 1000, and may have a shape of fine powder, pellet or the like. The titanium silicate can be prepared by a method disclosed in JP-A-56-96720.

In the present invention, such a titanium silicate can be used as a catalyst, and cyclohexanone is subjected to ammoximation with hydrogen peroxide and ammonia in the presence of the catalyst to obtain cyclohexanone oxime.

Cyclohexanone as a starting material may be obtained, for example, by oxidation of cyclohexane, by hydration of cyclohexene, followed by dehydrogenation, or by hydrogenation of phenol.

Hydrogen peroxide is usually produced by a so-called anthraquinone method and is commercially available in the form of an aqueous solution having a concentration of 10% by weight to 70% by weight, which may be utilized in the present invention. The relative molar amount of the hydrogen peroxide to be used is preferably in the range of from about 0.5 mol to about 3 mol, and is more preferably in the range of from about 0.5 mol to about 1.5 mol, based on 1 mol of the cyclohexanone.

The hydrogen peroxide to be used in the present invention may contain a stabilizer including, for example, a phosphate salt such as sodium phosphate, a polyphosphate salt such as sodium pyrophosphate, and sodium tripolyphosphate, pyrophosphoric acid, ascorbic acid, ethylenediamine-tetraacetic acid, nitro tri-acetic acid, amino tri-acetic acid, diethylenetriamino penta-acetic acid, and the like.

Ammonia may be used in a gaseous form, in a liquid form, or in a solution form of water, an organic solvent or the like.

The relative molar amount of the ammonia is preferably about 1 mol or more, and is more preferably about 1.5 mol or more, based on 1 mol of the cyclohexanone.

The ammoximation reaction in the present invention may be conducted in the presence of a solvent. Preferable examples of the solvent include an alcohol such as methyl alcohol, ethyl alcohol, n-propyl alcohol, isopropyl alcohol, n-butyl alcohol, sec.-butyl alcohol, tert.-butyl alcohol and tert.-amyl alcohol; water; and a mixture thereof.

In the present invention, the ammoximation reaction is carried out in the presence of a catalyst which has been used for ammoximation reaction and which may be degraded (hereinafter, referred to as "degraded catalyst" in some cases) as well as a catalyst which has not been used in the reaction (hereinafter, referred to as "brand-new catalyst" or "brand-new titanium silicate" in some cases).

By utilizing a degraded catalyst together with a brand-new catalyst, degradation of the brand-new catalyst, in particular, inactivation of the catalyst can be suppressed, and the amount of the brand-new catalyst can be reduced.

It is noted that the degraded catalyst itself may substantially have no catalytic activity as a catalyst for the ammoximation reaction, since the degraded catalyst is used in the reaction for suppressing the degradation of the brand-new catalyst, rather than for supplementing the catalytic activity of the brand-new catalyst.

A degraded catalyst may be obtained by recovering a used catalyst from the ammoximation reaction system, and is employed again in the reaction. When the reaction is conducted batch-wise, the degraded catalyst may be recovered by, for example, separating a used catalyst from the reaction mixture with filtration or decantation method after the reaction. When the reaction is conducted continuously, the degraded catalyst may be recovered by, for example, stopping the reaction after employing the reaction for a certain period of time and then separating a used catalyst from a mixture remaining in the reaction vessel (that is the reaction mixture) with filtration or decantation method.

The recovered catalyst may be washed with a solvent and/or may be calcined, if necessary, after being separated from the reaction mixture. Alternatively, the reaction mixture containing a degraded catalyst may be utilized as a degraded catalyst as it is, without conducting the separation step.

Thus-obtained used catalyst is utilized as a recycled titanium silicate in the present invention.

When the production method of a cyclohexanone oxime in the present invention is conducted in a batch-wise manner, the batch-wise reaction may be carried out, for example, by a method in which a reactor is charged with cyclohexanone, ammonia, a brand-new catalyst, a degraded catalyst and a solvent, into which hydrogen peroxide is introduced to conduct the reaction, while stirring; or by a method in which a reactor is charged with cyclohexanone, a brand-new catalyst, a degraded catalyst and a solvent, into which hydrogen peroxide and ammonia are introduced to conduct the reaction, while stirring; or by a method in which a reactor is charged with a brand-new catalyst, a degraded catalyst and a solvent, into which cyclohexanone, hydrogen peroxide and ammonia are introduced to conduct the reaction, while stirring.

When the production method of a cyclohexanone oxime in the present invention is conducted in a continuous manner, the continuous reaction may be carried out, for example, by a method in which a suspension liquid (a start-up liquid) of a brand-new catalyst and a degraded catalyst is introduced in a reactor, into which cyclohexanone, hydrogen peroxide, ammonia and a solvent are further introduced to conduct the reaction, while a liquid portion of the resulting reaction mixture is discharged through a filter from the reactor.

It is preferred to use a glass-lining reactor, a stainless steel reactor or the like in view of avoiding decomposition of hydrogen peroxide.

The brand-new catalyst and the degraded catalyst are preferably used with being suspended in the reaction mixture so that each concentration thereof may be in the range of from about 0.1% by weight to about 20% by weight (more preferably about 0.1% by weight to about 10% by weight) in terms of the liquid portion of the reaction mixture.

The ratio of the degraded catalyst to the brand-new catalyst may be in the range of about 0.01 part by weight to about 100 parts by weight, preferably about 0.1 part by weight to about 20 parts by weight, and more preferably about 0.2 part by weight to about 2 parts by weight. The effect of suppressing the degradation of the brand-new catalyst by the degraded catalyst is remarkable especially when water is present in the reaction mixture at a concentration of about 10% by weight or more.

In the present invention, the ammoximation reaction may be carried out in the presence of a silicon compound other than titanium silicate, together with the brand-new catalyst and the degraded catalyst. The silicon compound, in itself, may substantially have no catalytic activity in the ammoximation reaction.

Examples of the silicon compound other than the titanium silicate include a compound containing silicon and oxygen, such as a silica gel, a silicic acid and a silicate. A crystalline silica gel and a crystalline metallo-silicate, each of which has a zeolite-like structure, are preferably used as such a silicon compound.

The silicon compound other than the titanium silicate is preferably used in a concentration of from 0.1% by weight to 10% by weight based on the liquid portion of the reaction mixture.

The ammoximation reaction may be carried out at a temperature in the range of from about 50° C. to about 100° C. The reaction may be performed at a normal pressure, and is preferably under pressure in order to increase the solubility of ammonia into the liquid portion of the reaction mixture. In the case of conducting the reaction under pressure, the pressure may be adjusted by using an inert gas (for example, nitrogen gas, helium gas or the like).

The obtained reaction mixture may be subjected to a known post-treatment, if necessary. For example, the separation of the cyclohexanone oxime may be conducted in a manner such that the catalysts are separated from the reaction mixture by filtration or the like to obtain the liquid portion of the reaction mixture, followed by distillation of the liquid portion.

In accordance with the present invention, cyclohexanone is subjected to ammoximation by hydrogen peroxide and ammonia with suppressing the degradation of titanium silicate as a catalyst, to produce cyclohexanone oxime with a high yield.

The invention being thus described, it will be apparent that the same may be varied in many ways. Such variations are to be regarded as within the spirit and scope of the invention, and all such modifications as would be apparent to one skilled in the art are intended to be within the scope of the following claims.

The entire disclosure of the Japanese Patent Application No. 2003-104900 filed on Apr. 9, 2003, indicating specification, claims and summary, are incorporated herein by reference in their entirety.

EXAMPLE

The present invention is described in more detail by reference to the following Examples, which should not be construed as a limitation upon the scope of the present invention.

In Examples and Comparative Examples, the cyclohexanone and cyclohexanone oxime were analyzed by gas-chromatography, and conversion of cyclohexanone, selectivity to cyclohexanone oxime and yield of cyclohexanone oxime were calculated on the basis of the analytical results.

Reference Example 1 (Procedure for obtaining a degraded catalyst)

A brand-new catalyst (7 g), which had not been used in a reaction, was utilized as a titanium silicate in the following reaction.

A one (1) L autoclave as a reactor was charged with a cyclohexanone, a water-containing t-butyl alcohol (containing 12% by weight of water) and a 60% by weight of hydrogen peroxide at a rate of 67 g/hour, 252 g/hour and 43 g/hour, respectively. At the same time, ammonia was supplied into the reactor so as to be present at the concentration of 2% by weight based on the liquid portion of the resulting reaction mixture, while the liquid portion of the reaction mixture was discharged from the reactor through a filter, to conduct the reaction continuously. The continuous reaction was performed at a temperature of 85° C. under a pressure of 0.25 MPa with a retention time of 72 minutes. During the reaction, the reaction mixture in the reactor contained the titanium silicate in the amount of 1.4% by weight based on the liquid phase of the reaction mixture.

Sudden rise of oxygen concentration in the gas phase was observed due to the lowering of the catalytic activity, 29 hours later from the beginning of the reaction, and then, the reaction was stopped. The reaction mixture in the reactor was subjected to pressure filtration, to separate the catalyst. The separated catalyst was washed with t-butyl alcohol and then was dried under a nitrogen gas flow for 30 minutes. Thus-obtained degraded catalyst was employed in Example 1 below.

The liquid portion obtained after 24.5 hours of the reaction was analyzed. As a result, the conversion of the cyclohexanone was 91.3%, the selectivity to cyclohexanone oxime was 98.2% and the yield of cyclohexanone oxime was 89.6%.

Comparative Example 1

The reaction was conducted in the same manner as in Reference Example 1, except that the amount of the brand-new catalyst (which had not been used in a reaction) as a titanium silicate was changed to 5 g, and the relative amount of the titanium silicate was changed to 1.0% by weight based on the liquid portion of the reaction mixture.

Sudden rise of oxygen concentration in the gas phase was observed due to the lowering of the catalytic activity, 6 hours later from the beginning of the reaction. The liquid portion obtained after 5.5 hours of the reaction was analyzed. As a is result, the conversion of the cyclohexanone was 87.6%, the selectivity to cyclohexanone oxime was 90.4% and the yield of cyclohexanone oxime was 79.3%.

Example 1

The reaction was conducted in the same manner as in Reference Example 1, except that a brand-new catalyst (which had not been used in the reaction) (5 g) and the degraded catalyst (which had been used in the reaction and obtained in Reference 1) (2 g) were utilized as titanium silicates, and the relative amount in total of the titanium silicates was changed to 1.4% by weight (brand-new catalyst: 1.0% by weight, degraded catalyst: 0.4% by weight) based on the liquid portion of the reaction mixture.

Sudden rise of oxygen concentration in the gas phase was observed due to the lowering of the catalytic activity, 20 hours later from the beginning of the reaction.

The liquid portion obtained after 18.5 hours of the reaction was analyzed. As a result, the conversion of the cyclohexanone was 89.4%, the selectivity to cyclohexanone oxime was 95.9% and the yield of cyclohexanone oxime was 85.8%.

Comparative Example 2

The reaction is conducted in the same manner as in Reference Example 1, to obtain a degraded catalyst.

The same procedure as in Example 1 is conducted, except that the degraded catalyst (7 g) is utilized as titanium silicate instead of using the brand-new catalyst (5 g) and the degraded catalyst (2 g). The reaction, however, is not substantially carried out due to the lowering of the catalytic activity of the degraded catalyst.

What is claimed is:

1. A method for producing a cyclohexanone oxime, the method comprising the step of reacting cyclohexanone, hydrogen peroxide and ammonia in the presence of a brand-new titanium silicate and a recycled titanium silicate, wherein the recycled titanium silicate is a titanium silicate which has been recovered from a method comprising the step of reacting cyclohexanone, hydrogen peroxide and ammonia in the presence of titanium silicate.

2. The method according to claim 1, wherein the method is conducted in the presence of water at a concentration of about 10% by weight or more.

3. The method according to claim 1 or 2, wherein the method is conducted in the presence of a silicon compound other than titanium silicate.

4. The method according to claim 1 or 2, wherein the ratio of the recycled titanium silicate to the brand-new titanium silicate is in the range of from about 0.2 part by weight to about 2 parts by weight.

5. The method according to claim 1 or 2, the method further comprising a step of washing the recycled titanium silicate with a solvent after the recovery step.

6. The method according to claim 1, wherein the recycled titanium silicate is a titanium silicate that has been used for ammoximation reaction and is degraded.

7. The method according to claim 1, wherein the recycled titanium silicate substantially has no catalytic activity as a catalyst for the ammoximation reaction.

* * * * *